US00PP15914P2

(12) United States Plant Patent
Hooijman

(10) Patent No.: US PP15,914 P2
(45) Date of Patent: Aug. 9, 2005

(54) ***VERONICA* PLANT NAMED 'AMETHYST'**

(50) Latin Name: *Veronica spicata*
Varietal Denomination: Amethyst

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 8 days.

(21) Appl. No.: 10/888,914

(22) Filed: Jul. 9, 2004

(51) Int. Cl.[7] ..... A01H 5/00
(52) U.S. Cl. ..... Plt./251
(58) Field of Search ..... Plt./251

*Primary Examiner*—Anne Marie Grunberg
*Assistant Examiner*—Annette H Para
(74) *Attorney, Agent, or Firm*—C. A. Whealy

(57) ABSTRACT

A distinct cultivar of *Veronica* plant named 'Amethyst', characterized by its upright and uniform plant habit; vigorous growth habit; strong stems; relatively small leaves; freely flowering habit; and violet-colored flowers.

1 Drawing Sheet

Botanical classification/cultivar designation: *Veronica spicata* cultivar Amethyst.

BACKGROUND OF THE INVENTION

The present Invention relates to a new and distinct cultivar of *Veronica* plant, botanically known as *Veronica spicata,* and hereinafter referred to by the cultivar name Amethyst.

The new *Veronica* is a product of a planned breeding program conducted by the Inventor in El Quinche, Pichincha, Ecuador. The objective of the breeding program is to develop new dark blue-colored cultivars of *Veronica* with good stem and foliage quality.

The new *Veronica* plant originated from a cross-pollination of a proprietary selection of *Veronica spicata* identified as Code 07, not patented, as the female, or seed, parent with an unknown selection of *Veronica spicata,* not patented, as the male, or pollen, parent. The new *Veronica* was discovered by the Inventor in August, 1999 in a controlled environment in El Quinche, Pichincha, Ecuador.

Asexual reproduction of the new cultivar by cuttings in a controlled environment in El Quinche, Pichincha, Ecuador since April, 2000, has shown that the unique features of this new *Veronica* are stable and reproduced true to type in successive generations.

SUMMARY OF THE INVENTION

Plants of the cultivar Amethyst have not been observed under all possible environmental and cultural conditions. The phenotype may vary somewhat with variations in environment such as temperature and light intensity without, however, any variance in genotype.

The following traits have been repeatedly observed and are determined to be the unique characteristics of 'Amethyst'. These characteristics in combination distinguish 'Amethyst' as a new and distinct cultivar:

1. Upright and uniform plant habit.
2. Vigorous growth habit.
3. Strong stems.
4. Relatively small leaves.
5. Freely flowering habit.
6. Violet-colored flowers.

Compared to plants of the female parent selection, plants of the new *Veronica* are more vigorous, have shorter inflorescences, have larger flowers and have darker violet-colored flowers.

Plants of the new *Veronica* can be compared to plants of the *Veronica* cultivar Aquamarine, disclosed in a U.S. Plant patent application Ser. No. 10/888,915. In side-by-side comparisons conducted in El Quinche, Pichincha, Ecuador, plants of the new *Veronica* differed from plants of the cultivar Aquamarine in the following characteristics:

1. Plants of the new *Veronica* were shorter than plants of the cultivar Amethyst.
2. Plants of the new *Veronica* had longer inflorescences and larger flowers than plants of the cultivar Amethyst.

Plants of the new *Veronica* can also be compared to plants of the *Veronica* cultivar Verona, not patented. In side-by-side comparisons conducted in El Quinche, Pichincha, Ecuador, plants of the new *Veronica* differed from plants of the cultivar Verona in the following characteristics:

1. Plants of the new *Veronica* grew faster and flowered earlier than plants of the cultivar Verona.
2. Plants of the new *Veronica* had shorter inflorescences than plants of the cultivar Verona.
3. Plants of the new *Veronica* had larger flowers than plants of the cultivar Verona.
4. Plants of the new *Veronica* had darker violet-colored flowers than plants of the cultivar Verona.

BRIEF DESCRIPTION OF THE PHOTOGRAPH

The accompanying colored photograph illustrates the overall appearance of the new *Veronica,* showing the colors as true as it is reasonably possible to obtain in colored reproductions of this type. Colors in the photographs may differ slightly from the color values cited in the detailed botanical description which accurately describe the colors of the new *Veronica.*

The photograph comprises a side perspective view of a typical flowering stem of 'Amethyst'.

DETAILED BOTANICAL DESCRIPTION

In the following description, color references are made to The Royal Horticultural Society Colour Chart, 2001 Edition, except where general terms of ordinary dictionary significance are used. Plants used in the aforementioned photograph and for the following description were grown for about four to six months under outdoor field conditions which closely approximate commercial production conditions during the summer in Guayllabamba, Ecuador. During the production of the plants, day temperatures ranged from 12 to 30° C. and night temperatures ranged from 7 to 12° C.

Botanical classification: *Veronica spicata* cultivar Amethyst.

Parentage:

*Female, or seed, parent.*—Proprietary selection of *Veronica spicata* identified as Code 07, not patented.

*Male, or pollen, parent.*—Unknown selection of *Veronica spicata,* not patented.

Propagation:

*Type.*—By cuttings.

*Time to initiate roots.*—About 10 to 14 days at 17 to 25° C.

*Time to produce a rooted young plant.*—About four to five weeks at 17 to 25° C.

*Root description.*—Fibrous, fine; freely branching; color, 161A.

Plant description:

*Form.*—Perennial flowering plant; upright and uniform plant habit; inverted triangle; vigorous growth habit.

*Plant height.*—About 85 cm.

*Plant diameter.*—About 31.5 cm.

*Flowering stem description.*—Quantity per plant: About six flowering stems per plant develop per year. Length: About 70 cm. Diameter: About 5 mm. Internode length: About 5.4 cm. Strength: Strong. Texture: Pubescent. Color: 146C.

*Foliage description.*—Arrangement: Opposite, simple. Length: About 12.6 cm. Width: About 4.3 cm. Shape: Lanceolate. Apex: Acute. Base: Truncate. Margin: Serrate to biserrate. Texture, upper and lower surfaces: Pubescent; smooth to rugose. Venation pattern: Pinnate. Color: Developing foliage, upper surface: 137B. Developing foliage, lower surface: 138B. Fully expanded foliage, upper surface: 147A. Fully expanded foliage, lower surface: 191A. Venation, upper and lower surfaces: 146C. Petioles: Length: About 1.7 cm. Diameter: About 2 mm. Color: 146C.

Flower description:

*Appearance.*—Single salverform flowers; flowers arranged on terminal racemes. Flowers face mostly outwardly to drooping. Flowers not persistent.

*Quantity of flowers.*—Freely flowering habit, about 260 flowers develop per raceme.

*Natural flowering season.*—Plants flower year-round in Ecuador.

*Fragrance.*—Sweet.

*Flower longevity.*—On the plant: About three weeks. As a cut flower: About two weeks.

*Inflorescence length.*—About 16.4 cm.

*Inflorescence diameter.*—About 2.3 cm.

*Flower diameter.*—About 9 mm.

*Flower depth (height).*—About 1.2 cm.

*Flower buds.*—Length: About 7.3 mm. Diameter: About 2 mm. Shape: Ellipsoidal. Color: N88A.

*Corolla.*—Petal lobes per flower: About four; fused at the base. Length: About 8 mm. Width: About 5 mm. Shape: Salverform. Apex: Obtuse. Base: Fused. Margin: Entire. Texture, upper and lower surface: Smooth, glabrous. Color: When opening, upper and lower surfaces: N88A. Fully opened, upper and lower surfaces: N88A; color becoming closer to N199A to N199B with development.

*Calyx.*—Sepal lobes per flower: About four, fused at base. Arrangement: Rotate. Length: About 3.5 mm. Diameter: About 1.8 mm. Apex: Acute. Base: Fused. Margin: Entire. Texture, upper and lower surfaces: Pubescent. Color: When opening and fully opened, upper surface: 137C. When opening and fully opened, lower surface: 137C.

*Peduncles.*—Length: About 2.7 mm. Diameter: About 1.9 mm. Angle: About 64° from vertical. Strength: Strong. Color: 146C.

*Pedicels.*—Length: About 1.1 mm. Diameter: About 0.25 mm. Angle: About 28° from vertical. Strength: Strong. Color: N77A.

*Reproductive organs.*—Stamens: Quantity per flower: Two. Anther shape: Elliptic; curved. Anther length: About 1 mm. Anther color: N88B. Pollen amount: Abundant. Pollen color: 12B. Pistils: Quantity per flower: One. Style length: About 8 mm. Style color: N88B. Stigma shape: Roughly ovoid. Stigma color: Darker than N88B. Ovary color: 145A.

*Fruit.*—Quantity per flower: One. Length: About 3 mm. Diameter: About 2 mm. Texture: Hairy, crustaceous. Color: N199C.

*Seed.*—Quantity per fruit: About 12. Length: About 1 mm. Diameter: About 0.75 mm. Color: N199D.

Disease/pest resistance: Plants of the new *Veronica* have not been noted to be resistant to pathogens or pests common to *Veronica*.

Temperature tolerance: Plants of the new *Veronica* are tolerant to temperatures from about 7 to 30° C.

It is claimed:

1. A new and distinct cultivar of *Veronica* plant named 'Amethyst', as illustrated and described.

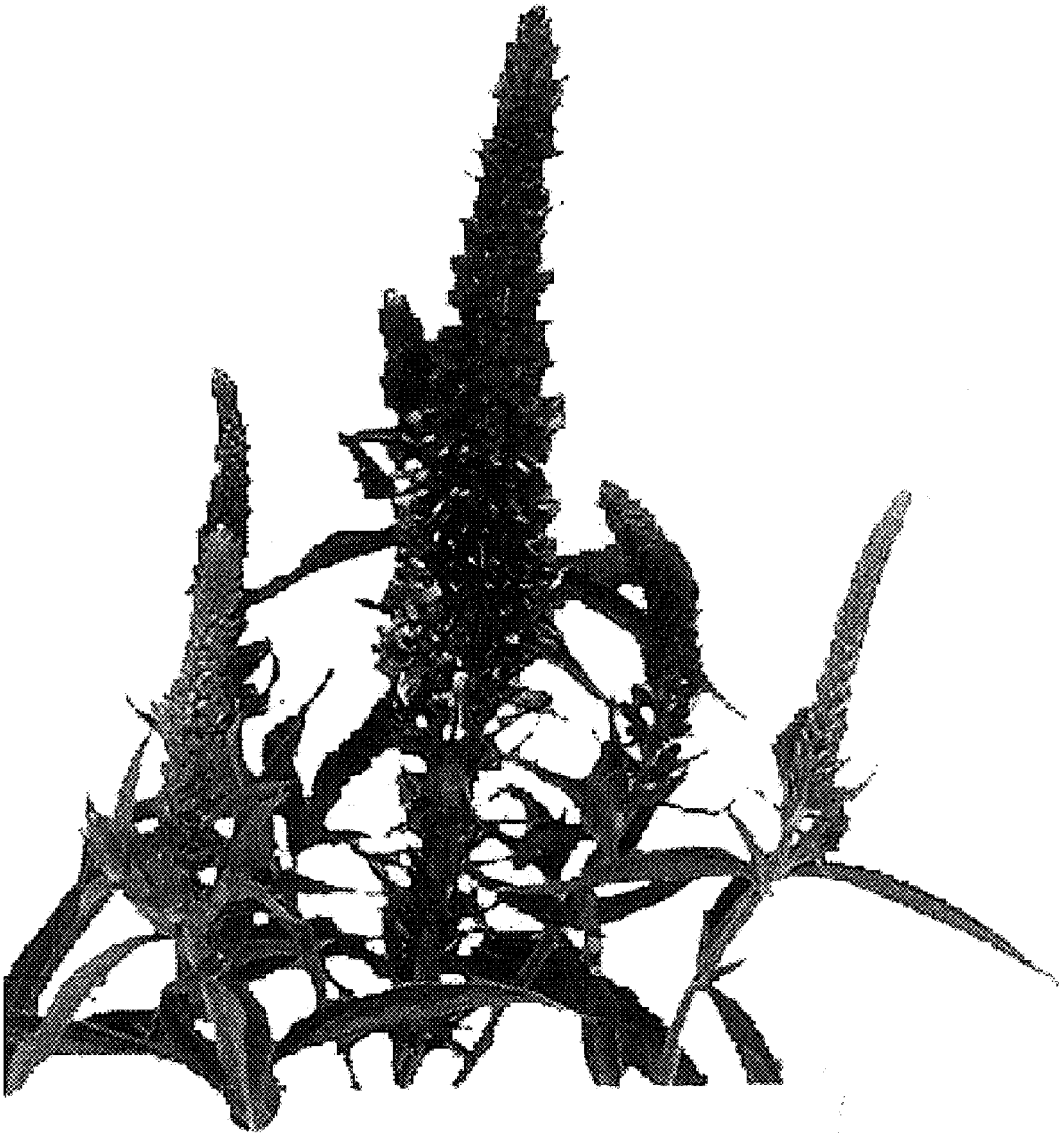

* * * * *